(12) United States Patent
Amano et al.

(10) Patent No.: US 7,708,874 B2
(45) Date of Patent: May 4, 2010

(54) ELECTROPHORESIS APPARATUS

(75) Inventors: Yoshinori Amano, Ehime (JP); Kazuyoshi Mori, Ehime (JP); Ryuuji Shimizu, Ehime (JP)

(73) Assignee: Panasonic Corporation, Osaka (JP)

( * ) Notice: Subject to any disclaimer, the term of this patent is extended or adjusted under 35 U.S.C. 154(b) by 568 days.

(21) Appl. No.: 11/652,562

(22) Filed: Jan. 12, 2007

(65) Prior Publication Data

US 2007/0163885 A1   Jul. 19, 2007

(30) Foreign Application Priority Data

Jan. 13, 2006   (JP) .............................. 2006-006762

(51) Int. Cl.
*C02F 11/00* (2006.01)
*C02F 1/40* (2006.01)
(52) U.S. Cl. ..................... 204/601; 204/602; 204/603
(58) Field of Classification Search ......... 204/600–603, 204/607, 612, 621
See application file for complete search history.

(56) References Cited

U.S. PATENT DOCUMENTS 5,847,405 A * 12/1998 Acquaviva et al. ..... 250/559.36

FOREIGN PATENT DOCUMENTS

| EP | 0 671 626 | 9/1995 |
|---|---|---|
| EP | 1 712 916 | 10/2006 |
| JP | 7-311198 | 11/1995 |
| JP | 2000-513813 | 10/2000 |
| JP | 2000-514928 | 11/2000 |
| JP | 2001-523341 | 11/2001 |
| JP | 2003-28883 | 1/2003 |
| WO | 98/00707 | 1/1998 |
| WO | 98/49548 | 11/1998 |
| WO | 98/53311 | 11/1998 |
| WO | 2005/064339 | 7/2005 |

* cited by examiner

*Primary Examiner*—Nam X Nguyen
*Assistant Examiner*—Gurpreet Kaur
(74) *Attorney, Agent, or Firm*—Wenderoth, Lind & Ponack, L.L.P.

(57) ABSTRACT

An electrophoresis apparatus having a plate on which channels are formed, a tray on which the plate is to be set, a tray driving unit for rotary driving the tray on which the plate is set, a voltage application unit for applying voltage to a buffer agent in the channels on the plate, an optical detection part for irradiating the channels on the plate with light, and detecting fluorescence that is generated from the sample due to the light irradiation. A plate clamp pressing the plate at only the channel formation areas of the plate against the plate setting surface of the tray, thereby fixing and holding the plate on the plate setting surface of the tray.

12 Claims, 12 Drawing Sheets

US 7,708,874 B2

ELECTROPHORESIS APPARATUS

FIELD OF THE INVENTION

The present invention relates to an electrophoresis apparatus which is suitable for moving a biological sample such as DNA, protein, or the like in a buffer agent, and detecting its transport reaction to analyze the biological sample.

BACKGROUND OF THE INVENTION

When general biological samples are considered, there exist DNAs and proteins broadly. In recent years, with rapid progress in chemical biology, involvement of genes in various diseases has been understood with a fair degree of precision, and medical cares targeted at genes have attracted attention. With respect to DNA, SNPs (which is an abbreviation of single nucleotide polymorphisms, and a general term for a difference of a single code (a single nucleotide) in genes) attract attention presently. The reason is as follows. By classifying SNPs, it is possible to predict the prevalence rates of many diseases, and the effects or sensitivities of individuals to medical agents, and furthermore, it is possible to perform perfect identification of an individual because there never exist plural human beings having completely the same SNPs on the planet, even parent and child or brothers.

Presently, as a method for examining SNPs, sequencing (determination of a base sequence) by which a DNA base sequence is directly read from an end, has been employed most commonly. While several methods of performing the sequencing have been reported, a dideoxy method (Sanger method) has been carried out most commonly. The sequencing is, in any method including the Sanger method, based on a technique for separating/discriminating a difference in single base lengths by modified polyacrylamide gel electrophoresis having a high separation capability, or capillary electrophoresis.

As another method, there is affinity ligand capillary electrophoresis.

The affinity ligand capillary electrophoresis makes separation have specificity, utilizing intermolecular affinity, especially, specific affinity in ecosystem (enzyme-substrate affinity, antigen-antibody affinity, or the like). To be specific, analysis is carried out with an attention on a phenomenon that, when a sample migrates electrophoretically in an electrophoresis solution in a capillary tube, to which an affinity ligand that specifically recognizes a base sequence is added, only molecular species that mutually react in the sample mixture have variations in migration speeds (for example, refer to Japanese Published Patent Application No. Hei. 7-311198 (Patent Document 1)).

On the other hand, proteins exist in cells, tissues, and bio-fluids, and are involved in control of organic activities, supply of energies to cells, synthesis of important substances, maintenance of organic structures, and further, inter-cell communication and intra-cell communication. Recently, it has increasingly become clear that proteins have plural functions according to various environments, existences of other proteins for mutual reaction, degrees and kinds of modifications given to proteins.

Proteins are produced by sequentially connecting twenty kinds of amino acids according to instructions of genes (sequence information), and it is said that there are tens of millions of proteins. If the genetic sequence is found, information as to what amino acids are connected in what order can be obtained. A set of proteins produced by instructions of biotic genes (genomes) is called proteome, and analysis of proteome is actively carried out now upon completion of sequencing of human genomes.

With respect to analysis and study for functions of proteins, it is necessary to perform, not only identification and characterization, but also biochemical assay, investigation for inter-protein reactions, elucidation of protein network, and elucidation of signaling in and out of cells. Various fields of technologies are adopted for the study of protein functions, for example, enzyme assay, yeast two-hybrid assay, purification by chromatography, information tool and data base, and the like. Particularly, discrimination of proteins by electrophoresis is an important scheme. There are various reports relating to fluid transportation and orientation in the case where sample analysis, discrimination, determination, and the like are carried out by detecting a transport reaction obtained when a fluid in a capillary tube, such as a sample, an analyte, a buffer agent, or a reagent is electrophoretically migrated (for example, refer to Japanese Unexamined Patent Publication No. 2000-513813 (Patent Document 2), Japanese Unexamined Patent Publication No. 2001-523341 (Patent Document 3), Japanese Unexamined Patent Publication No. 2000-514928 (Patent Document 4), Japanese Published Patent Application No. 2003-28883. (Patent Document 5)).

In recent years, an electrophoresis apparatus using a biological sample discrimination plate as disclosed in a brochure of International Publication No. 2005/064339 (Patent Document 6) has been also reported besides the above-mentioned capillary electrophoresis apparatus.

FIG. 10 is a diagram illustrating the construction of the conventional electrophoresis apparatus disclosed in the Patent Document 6, and the electrophoresis apparatus 400 uses a plastic biological sample discrimination plate 10 (hereinafter referred to simply as "plate") on which fine channels are formed. When performing discrimination, the plate 10 on which a DNA sample and a DNA conjugate for separation are injected into the channels is mounted on a tray 422, and the plate 10 is rotated at a high speed by a high-speed rotation motor 421 to fill a portion of the channel with the DNA conjugate for separation, and thereafter, a predetermined position of the channel is pressurized by a pressurization unit 424, and further, the plate 10 is again rotated by the high-speed rotation motor 421, whereby a predetermined amount of the DNA sample is added to the DNA conjugate for separation that is filled in the channel. Then, the plate 10 is moved up by an elevation stage 450 that is vertically driven by a motor 451 to determine the position of the plate 10 with respect to an optical detection part 440 by a fitting pin 434, and further, the plate 10 is fixed by a clamper 436, and voltage application means 432a and 432b are inserted in a predetermined position of the channel on the plate 10. In this state, a predetermined potential gradient is applied to the DNA conjugate for separation by the voltage application means 432a and 432b to make the DNA sample migrate electrophoretically in the DNA conjugate for separation, and simultaneously, a fluorescent material added to the DNA sample that migrates electrophoretically in the channel on the plate 10 is irradiated with light from a laser or an LED while rotating the plate 10 by a low-speed rotation motor 431, and intensity distribution of fluorescence emitted from the fluorescent material is detected by the optical detection part 440. Accordingly, in the conventional electrophoresis apparatus 400, when the user injects the DNA sample and the DNA conjugate for separation into the plate 10 and sets the plate 10 of the apparatus 400, all the processings, i.e., filling of the DNA sample and the DNA conjugate for separation into the channel on the plate 10, electrophoresis of the DNA sample, and optical detection, are automatically carried out at the apparatus 400 side, whereby complicated preparation works are dispensed with, and accurate detection results can be obtained in short time.

In the above-mentioned conventional electrophoresis apparatus 400, however, since the optical detection part 440 performs scanning along the channel while rotating the plate 10 by the low-speed rotation motor 431 in the state where the voltage application means 432a and 432b for electrophoresis are pressed against the plate 10, the mechanism for rotating the voltage application means 432a and 432b and the plate 10 integrally is complicated, resulting in an increase in the scale of the apparatus.

Further, in the conventional electrophoresis apparatus 400, since high voltage for electrophoresis must be applied to the plate 10 from the voltage application means 432a and 432b while rotating the plate 10 by the low-speed rotation motor 431, the power supply mechanism is complicated, also resulting in an increase in the scale of the apparatus.

Further, in the conventional electrophoresis apparatus 400, since the DNA sample in the channel is optically detected while applying voltage to the plate 10 and rotating the plate 10 at a low speed as described above, if the positioning precision of the rotation center between the plate 10 and the voltage application means 432a and 432b is insufficient, the detection performance of the optical detection part 440 is degraded.

SUMMARY OF THE INVENTION

The present invention is made to solve the above-described problems and has for its object to provide a small, lightweight, and inexpensive electrophoresis apparatus which is easy to handle, and provides accurate detection results in relatively short time.

Other objects and advantages of the invention will become apparent from the detailed description that follows. The detailed description and specific embodiments described are provided only for illustration since various additions and modifications within the scope of the invention will be apparent to those of skill in the art from the detailed description.

In order to solve the above-mentioned problems, according to the present invention, there is provided an electrophoresis apparatus for adding a sample into channels, making the sample electrophoretically migrate by voltage application, and optically detecting the sample, which apparatus comprises: a plate on which the channels are formed; a tray on which the plate is set; a voltage application means having voltage application electrodes for applying voltage to the sample in the channels on the plate; a tray driving means for rotary driving the tray on which the plate is set; an optical detection part having a light irradiation means for irradiating the sample in the channels with light, and an optical detection means for detecting light which is emitted from the sample when the sample is irradiated with the light from the light irradiation means; a plate holding member for pressing only the channel formation areas of the plate against the plate setting surface of the tray, thereby fixing and holding the plate on the plate setting surface of the tray; and a voltage application contact/separation means for making the voltage application electrodes of the voltage application means contact with or apart from predetermined positions of the plate; wherein the voltage application electrodes of the voltage application means are brought into contact with the predetermined positions of the plate by the voltage application contact/separation means to make the sample migrate electrophoretically by voltage application, and thereafter, the voltage application electrodes of the voltage application means are separated from the predetermined positions of the plate by the voltage application contact/separation means, and the light emitted from the sample in the channels on the plate is detected by the optical detection part.

Therefore, during optical detection, distance precision between the optical detection part and the plate on which the channels are formed can be accurately achieved, whereby more accurate detection results can be obtained. Further, since positioning of the rotation center of the plate is easily carried out, complicated preparation works are dispensed with, and the detection results can be obtained in relatively short time. Furthermore, since the voltage application and the optical detection are carried out not simultaneously but alternately, the construction of the apparatus can be miniaturized and simplified.

According to the present invention, in the above-described electrophoresis apparatus, a predetermined amount of the sample is added to a buffer agent filled in the channels, and voltage is applied to the buffer agent by the voltage application electrodes of the voltage application means to make the sample migrate electrophoretically.

Since the buffer agent is used, more accurate detection results can be obtained.

According to the present invention, the above-described electrophoresis apparatus further includes a temperature control chamber for controlling the temperature surrounding the plate to a predetermined temperature.

Therefore, the periphery of the plate can be set at a predetermined temperature, whereby more accurate detection results can be obtained.

According to the present invention, in the above-described electrophoresis apparatus, the optical detection means detects fluorescence that is generated from the sample due to light irradiation.

Since the fluorescence generated from the sample is detected, more accurate detection results can be obtained.

According to the present invention, in the above-described electrophoresis apparatus, the plate holding member has a covex configuration in which its center portion projects relative to its circumference portion, and presses the plate against the plate setting surface of the tray by the circumference portion.

Therefore, warpage or lifting that occurs due to conditions during fabrication of the plate can be efficiently reduced, whereby the distance between the electrophoresis channels formed on the plate and the optical detection part can be set at a constant precision.

According to the present invention, in the above-described electrophoresis apparatus, the temperature control chamber contains the tray, and a heating/cooling device for controlling the plate temperature control chamber at a predetermined temperature, and has an aperture through which the plate can be attached/detached to/from the tray, which aperture is closed by a partial element of the voltage application means which is disposed on the temperature control chamber.

Therefore, the partial element of the voltage application means can function as a lid member of the temperature control chamber, whereby the construction of the apparatus can be miniaturized and simplified.

According to the present invention, in the above-described electrophoresis apparatus, the voltage application means has plural first elastic members which press partial members of the voltage application means at predetermined positions against the temperature control chamber.

Since the temperature control chamber can be hermetically closed with reliability, the temperature around the plate can be controlled with accuracy.

According to the present invention, in the above-described electrophoresis apparatus, the voltage application means makes the voltage application electrodes of the voltage application means contact with or apart from predetermined positions of the plate by the voltage application contact/separation means, in the state where the aperture of the temperature control chamber through which the plate can be attached/detached to/from the tray is closed with a partial element of the voltage application means.

Therefore, the voltage application electrodes of the voltage application means can be brought into contact with predetermined positions of the plate in the state where the temperature control chamber is hermetically closed with reliability, whereby more accurate detection results can be obtained.

According to the present invention, in the above-described electrophoresis apparatus, an optical lens constituting a part of the optical detection means is disposed in the temperature control chamber.

Therefore, light shielding and temperature control at the periphery of the optical lens can be reliably carried out in the apparatus.

According to the present invention, in the above-described electrophoresis apparatus, the plate setting surface of the tray has plural apertures so that the light which is emitted from the light irradiation means to the plate is not obstructed.

Therefore, the light emitted from the light irradiation means can be guided onto the plate without blocking the optical path.

According to the present invention, in the above-described electrophoresis apparatus, the apertures are provided through the tray at areas where the light radiated to the channels which are formed on the plate is not obstructed.

Therefore, the irradiation of light to the channels formed on the plate as well as the excitation light emitted from the channels are not obstructed, and thereby accurate optical detection is carried out.

According to the present invention, in the above-described electrophoresis apparatus, the voltage application electrodes of the voltage application means comprise probes having second elastic members for pressing the probes against the plate being embedded, and the probes apply voltages to predetermined positions of the channels formed on the plate.

Therefore, the probes serving as the voltage application electrodes of the voltage application means can be accurately brought into contact with the predetermined positions of the plate.

According to the present invention, in the above-described electrophoresis apparatus, the total of the forces of the plural first elastic members that elastically support the entire mechanism of the voltage application means is larger than the total of the forces of the plural second elastic members that are embedded in the probes as the plural voltage application electrodes, and the voltage application means is pressed in a two-stage construction by the plural first elastic members and the plural second elastic members, in the direction where the voltage application means presses the plate or in the direction where the voltage application means is separated from the plate.

Therefore, the probes serving as the voltage application electrodes of the voltage application means can be reliably brought into contact with the plate surface, whereby the voltage can be accurately applied to the sample in the channels during electrophoresis.

According to the electrophoresis apparatus of the present invention, on the tray on which the plate having channels is set, the plate holding member for fixing and holding the plate onto the plate setting surface of the tray is disposed, and the plate is pressed at only the channel formation areas of the plate by the plate holding member so as to fix and hold the plate onto the plate setting surface of the tray. Therefore, warpage and lifting of the plate can be efficiently suppressed, and the distance precision between the channels formed on the plate and the optical detection unit can be achieved, resulting in accurate detection results.

Furthermore, according to the electrophoresis apparatus of the present invention, there is provided the voltage application contact/separation means for making the voltage application electrodes contact with or apart from predetermined positions of the plate, and the electrophoresis operation by the voltage application means and the optical detection by the optical detection unit are alternately carried out. Therefore, the mechanism for rotating the tray and the voltage application means having the voltage application electrodes integrally is dispensed with, whereby the construction of the electrophoresis apparatus can be simplified and miniaturized.

BRIEF DESCRIPTION OF THE DRAWINGS

FIG. 3(*b*) is a diagram illustrating the construction of a tray according to the first embodiment.

FIG. 3(*c*) is a cross-sectional view illustrating the state where a plate is fixed and held by the plate clamp and the tray according to the first embodiment.

FIG. 6(*b*) is a diagram illustrating the vertical move of the electrode probe substrate by the voltage application contact/separation means according to the first embodiment, wherein the electrode probes contact the plate.

FIG. 8(*b*) is a diagram illustrating the state of the intermediate step where a predetermined amount of DNA sample is added to the DNA conjugate for separation that is filled in the channel formed on the plate according to the first embodiment.

FIG. 8(*c*) is a diagram illustrating the state where a predetermined amount of DNA sample is added to the DNA conjugate for separation that is filled in the channel formed on the plate according to the first embodiment.

DETAILED DESCRIPTION OF THE INVENTION

Embodiment 1

Hereinafter, an electrophoresis apparatus 100 according to a first embodiment of the present invention will be described.

The present invention realizes reductions in size, weight, and price of an electrophoresis apparatus which makes a biological sample migrate in a buffer agent, thereby to perform biological, enzymatical, immunological, and chemical assay.

In this first embodiment, in order to specify the description, it is assumed that the biological sample is a DNA sample, and the buffer agent includes a DNA conjugate for separation and a DNA bonding control agent (hereinafter referred to simply as "DNA conjugate for separation"). The electrophoresis apparatus 100 adds a predetermined quantity of the DNA sample into the DNA conjugate for separation which is filled in a channel to make the DNA sample migrate electrophoretically in the conjugate, and detects fluorescence intensity or absorbance in the channel to determine whether SNPs (Single Nucleotide Polymorphisms) of the DNA sample exist or not.

Figure 1:
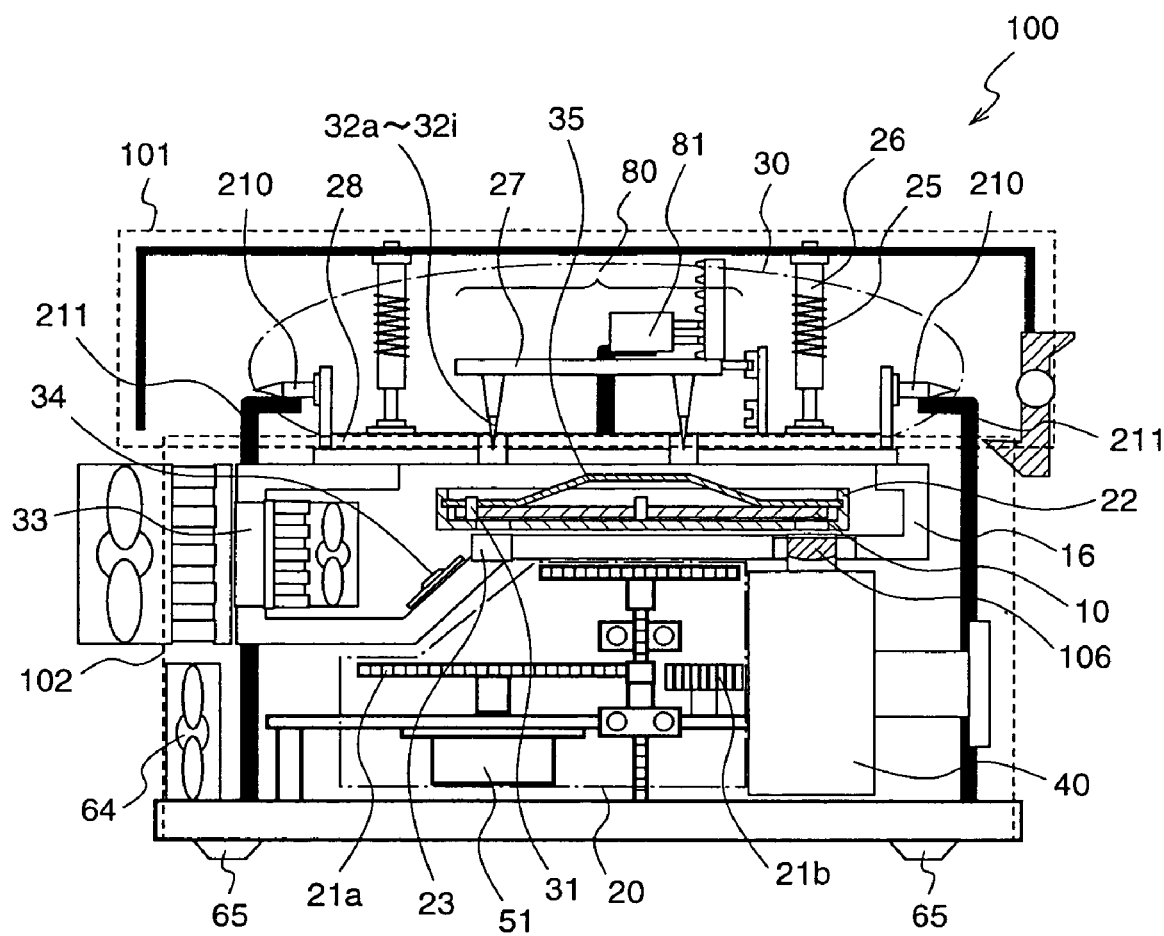
FIG. 1 is a diagram illustrating the construction of an electrophoresis apparatus according to a first embodiment of the present invention.

Initially, the construction of the electrophoresis apparatus 100 according to the first embodiment will be described with reference to FIGS. 1~4. FIG. 1 is a cross-sectional view illustrating the construction of the electrophoresis apparatus 100 according to the first embodiment.

With reference to FIG. 1, the electrophoresis apparatus 100 adds a predetermined amount of the DNA sample into the DNA conjugate for separation that is filled in channels 110, makes the DNA sample migrate electrophoretically in the DNA conjugate by applying voltage, and optically detects the DNA sample. The electrophoresis apparatus 100 comprises a tray 22 on which a plate 10 having the channels 110 is set, a tray driving means 20 for rotary driving the plate 10 as well as the tray 22, a voltage application means 30 having electrode probes 32a~32i as examples of voltage application electrodes for applying voltage to the DNA conjugate for separation that is filled in the channels 110 on the plate 10, and an optical detection part 40 which irradiates the channels 110 with light, and detects fluorescence intensity or absorbance of the DNA sample due to the light irradiation by using an objective lens 106, thereby to detect the migration state of the DNA sample in the DNA conjugate for separation, which DNA sample migrates due to the voltage application.

Figure 5:
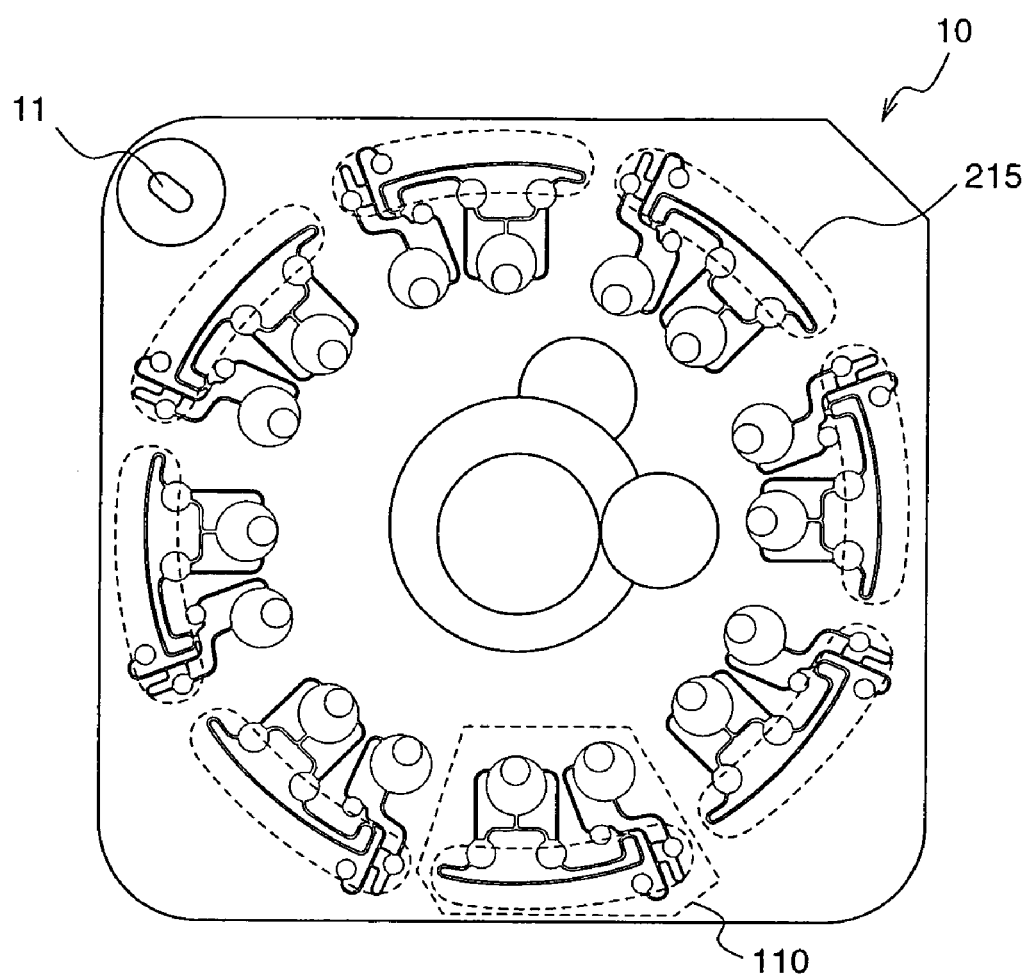
FIG. 5 is a diagram illustrating a channel formation surface of the plate according to the first embodiment.

As shown in FIG. 5, plural channels 110 are concentrically formed on the plate 10, and the plate 10 is set on the tray 22 with its surface on which the channels are formed facing the tray 22. Further, at this time, the plate 10 is set so that a fitting pin 31 provided on the tray 22 is fitted in a fitting hole 11 provided on the plate 10. Thereby, the plate 10 is position-determined with respect to the tray 22.

By the way, the planarity of the plate 10 somewhat varies due to the conditions when it is fabricated, and consequently, when the plate 10 is set on the tray 22, the optical distance between the channel formation surface of the plate 10 and the objective lens 106 of the optical detection part 40 sometimes varies. Since this variation in the optical distance adversely affects the optical detection performance of the optical detection part 40, it is necessary to set the distance between the optical detection part 40 and the plate 10 at a constant precision.

Accordingly, in this first embodiment, in order to achieve the distance precision between the plate 10 and the objective lens 106, there is provided, as a plate holding member, a plate clamp 35 for holding down only portions of the surface of the plate 10 in the vicinity of channel formation areas in which channels for electrophoresis 110a are formed (areas 215 in FIG. 5).

Thereby, warpage and lifting of the plate 10 can be efficiently held down, and the distance precision between the electrophoresis channel 110a on the plate 10 and the objective lens 106 can be achieved.

Figure 3A:
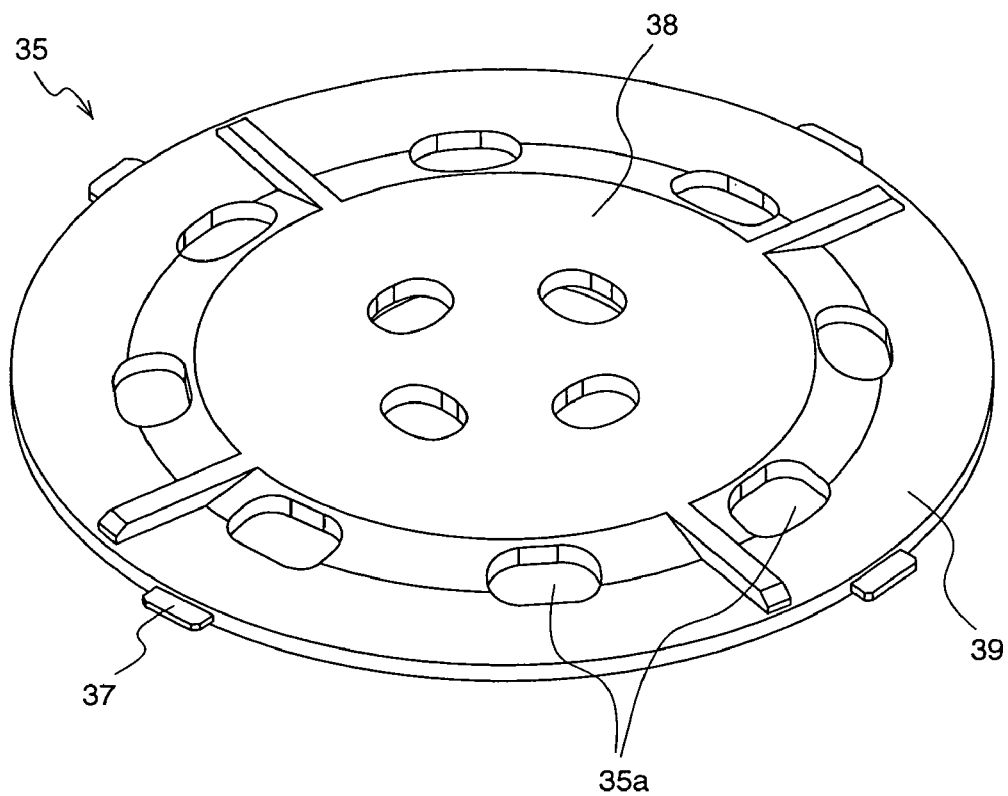
FIG. 3(*a*) is a diagram illustrating the construction of a plate clamp according to the first embodiment.
Figure 3B:
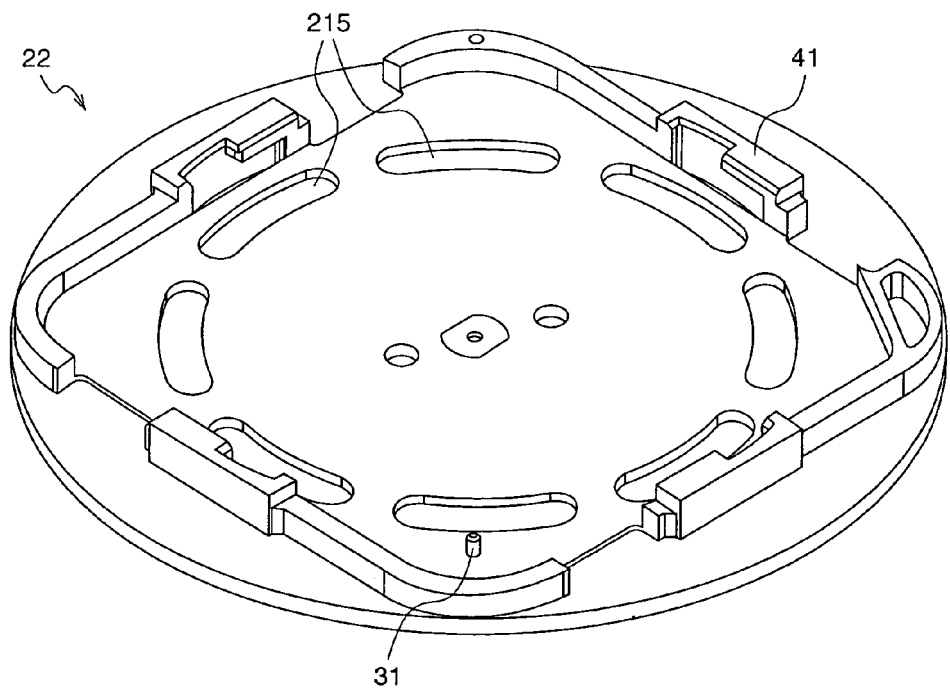

Hereinafter, the structures of the plate clamp 35 and the tray 22 in the electrophoresis apparatus 100 according to the first embodiment will be described with reference to FIGS. 3(a)-3(c). FIG. 3(a) is a diagram illustrating the structure of the plate clamp, FIG. 3(b) is a diagram illustrating the structure of the tray, and FIG. 3(c) is a cross-sectional view illustrating the state where the plate is fixed and held by the tray and the plate clamp.

As shown in FIG. 3(a), the plate clamp 35 has a convex configuration in which its center portion 38 projects relative to its circular ring portion 39, and plural clamp projections 37 for latching the plate clamp 35 to the tray 22 are provided at the outer circumference of the plate clamp 35. Further, the plate clamp 35 is provided with plural probe holes 35a through which the electrode probes 32a~32i can contact a conductive film 12 (refer to FIG. 3(c)) that is attached to the upper surface of an electrode part (not shown) formed on the plate 10. When the film 12 is nonconductive, the electrode probes 32 puncture the film 12 and get into the electrode part of the channel to apply voltage.

Figure 3C:
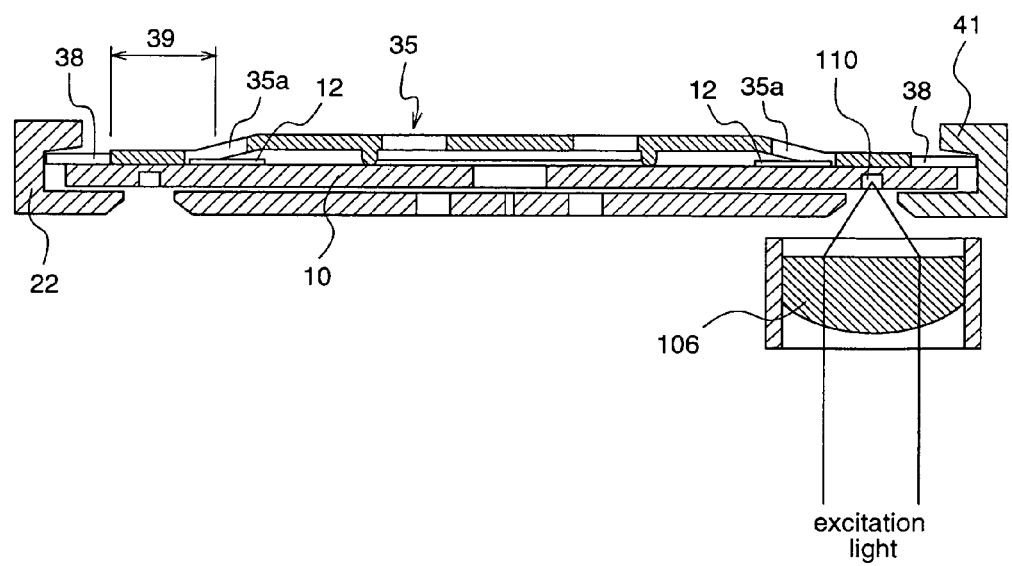

The above-mentioned plate clamp 35 is put on the tray 22 on which the plate 10 is set as shown in FIG. 3(c), and latch portions 41 provided on the tray 22 are fitted to the clamp projections 37 provided on the plate clamp 35, whereby the plate 10 can be fixed to and held on the plate setting surface of the tray 22 while correcting the planarity of the plate 10.

Further, since the plate clamp 35 has the convex configuration in which the center portion 38 projects relative to the circular ring portion 39 so that the contact surface of the plate clamp 35 to the plate 10 becomes a planar surface having an approximately circular ring shape as shown in FIG. 3(c), it is possible to hold down only the portions in the surface of the plate 10 in the vicinity of the concentrically formed electrophoresis channels 110a. As a result, the distance precision between the objective lens 106 and the channel formation surface of the plate 10, especially, the plate surface in the vicinity of the electrophoresis channels 110a, is achieved, thereby assuring the optical detection performance of the optical detection part 40.

Further, as shown in FIG. 3(b), the tray 22 is provided with plural apertures 215 at least as many as the number of the channels 110 formed on the plate 10, for irradiating the plate 10 with light emitted from the optical detection part 40. In this first embodiment, since the apertures 215 of the tray 22 are formed only in the positions opposed to the areas of the electrophoresis channels 110a, desired performance can be secured without significantly reducing the bending strength of the tray 22.

Figure 4:
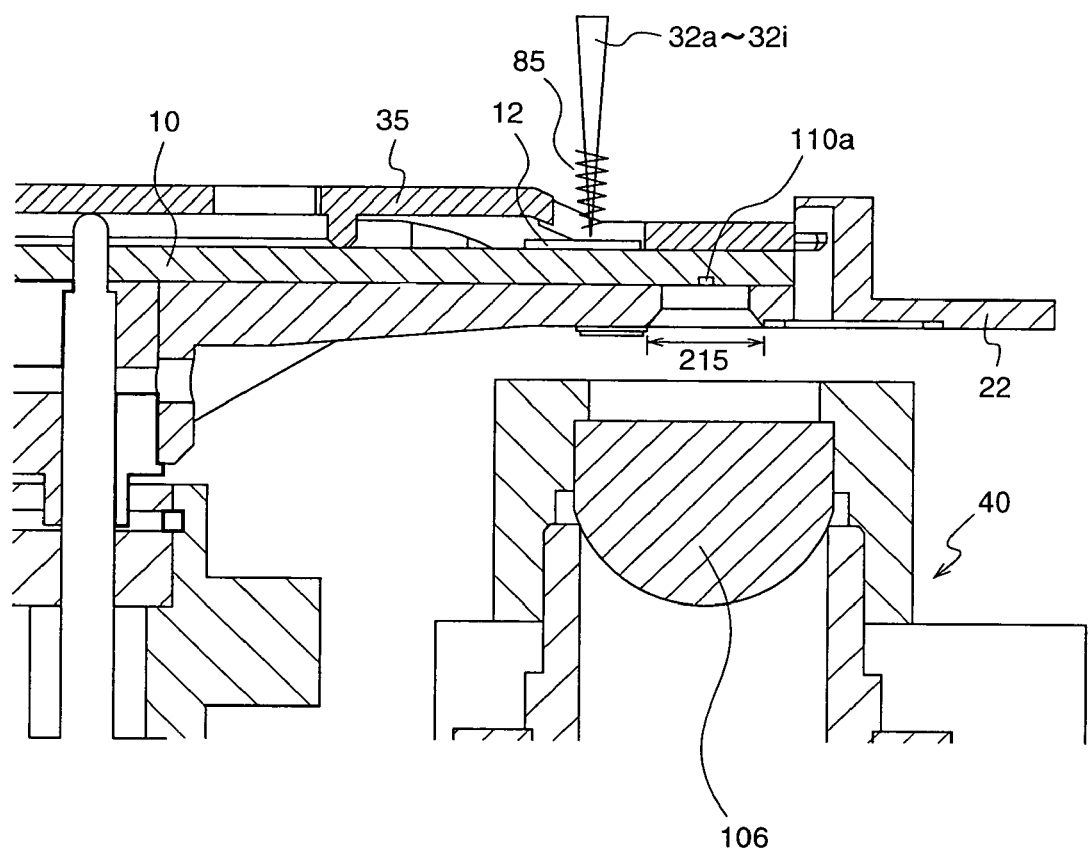
FIG. 4 is a diagram illustrating the positional relationships among an electrophoresis channel on the plate, an electrode probe, and an aperture of the tray, according to the first embodiment.

FIG. 4 is a diagram illustrating the aperture of the tray according to the first embodiment in more detail. With reference to FIG. 4, as for a width of the aperture 215 of the tray, it is desired to secure a width that does not prevent the light emitted from the optical detection part 40 through the objective lens 106 from reaching the electrophoresis channel 110a on the plate 10, and that does not prevent the light (fluorescence) emitted from the electrophoresis channel 110a from reaching the objective lens 106 of the optical detection part 40, and specifically, it is desired to secure a width of about 3 mm or more from the center axis of the electrophoresis channel 110a.

Further, in this first embodiment, the periphery of the plate 10 and the tray 22 is surrounded with a plate temperature control chamber 16 for keeping the temperature surrounding the plate 10 constant. Further, an aperture for attaching/detaching the plate 10 is provided at the upper surface of the plate temperature control chamber 16, and a heating/cooling device 33 for keeping the plate temperature control chamber 16 at a predetermined temperature, and a thermistor 34 for detecting the ambient temperature of the plate 10 are disposed in the temperature control chamber 16.

Although the plate temperature control chamber 16 is desired to have an aperture so that the light emitted from the optical detection part 40 disposed beneath the control chamber 16 or the light (fluorescence) emitted from the channels on the plate 10 is not blocked by the temperature control chamber 16, the aperture should be as small as possible to accurately control the temperature surrounding the plate 10. Accordingly, in this first embodiment, as shown in FIG. 1, among the constituents of the optical detection part 40, only the objective lens 106 for detecting the luminescence (fluorescence) from the channels is disposed inside the plate temperature control chamber 16 while other members are disposed outside the plate temperature control chamber 16. Since the optical detection part 40 and the tray driving means 20 are disposed not inside but outside the plate temperature control chamber 16, the volume of the plate temperature control chamber 16 is minimized, resulting in more accurate temperature control.

Depending on the focal distance of the objective lens 106, a portion of the optical detection part 40 may be inserted in the plate temperature control chamber 16 (not shown). In this case, in order to minimize the portion, the shape of an aperture to be formed on a wall of the plate temperature control chamber 16 between the tray 22 and the optical detection part 40 should be suited to the shape of the portion to be inserted.

The tray driving means 20 contains, as a mechanism for rotating the tray 22, a motor 51 as a driving source, a high-speed rotation switching gear 21a for rotating the tray 22 at a high speed, and a low-speed rotation switching gear 21b for rotating the tray 22 at a low speed. The high-speed rotation switching gear 21a and the low-speed rotation switching gear 21b are provided so as to be switchable with respect to the motor 51, thereby enabling high-speed rotation and low-speed rotation of the tray 22 by the motor 51.

The voltage application means 30 is provided with plural electrode probes 32a~32i for applying voltage, an electrode probe substrate 27 on which the plural electrode probes 32 are electrically connected and fixed, and a voltage application contact/separation means 80 for making the electrode probe substrate 27 contact with or apart from the plate 10. The voltage application contact/separation means 80 includes a driving motor 81 such as a DC motor, and an electrode height detection sensor 82 for detecting the position of the electrode probe substrate 27 that is driven by the driving motor 81, whereby the electrode probe substrate 27 is vertically moved between predetermined positions to enable contact or separation of the electrode probes 32 to/from the plate 10. Further, each electrode probe 32 has, at its front end, an embedded spring 85 such as a compression spring for adjusting the contact pressure when the electrode probe 32 is brought into contact with the plate 10 by the voltage application contact/separation means 80.

Figure 6A:
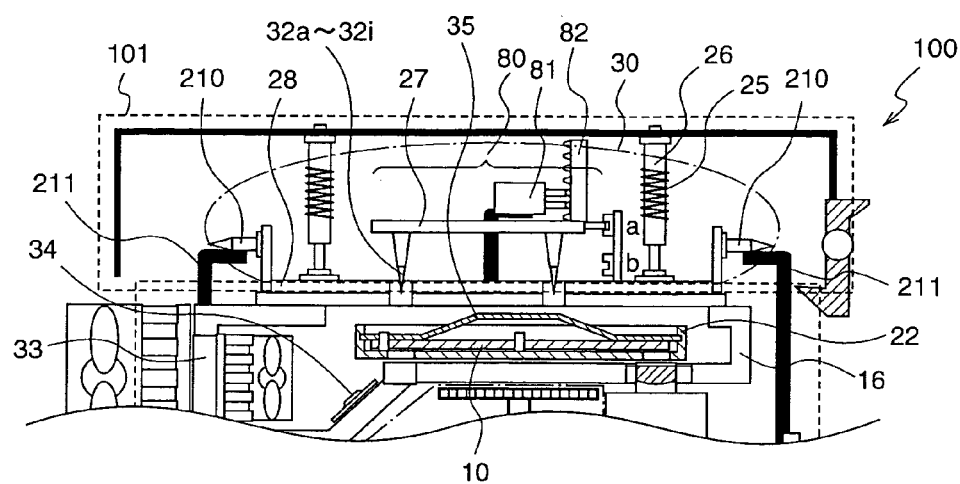
FIG. 6(*a*) is a diagram illustrating the vertical move of an electrode probe substrate by a voltage application contact/separation means according to the first embodiment, wherein the electrode probes are separated from the plate.
Figure 6B:
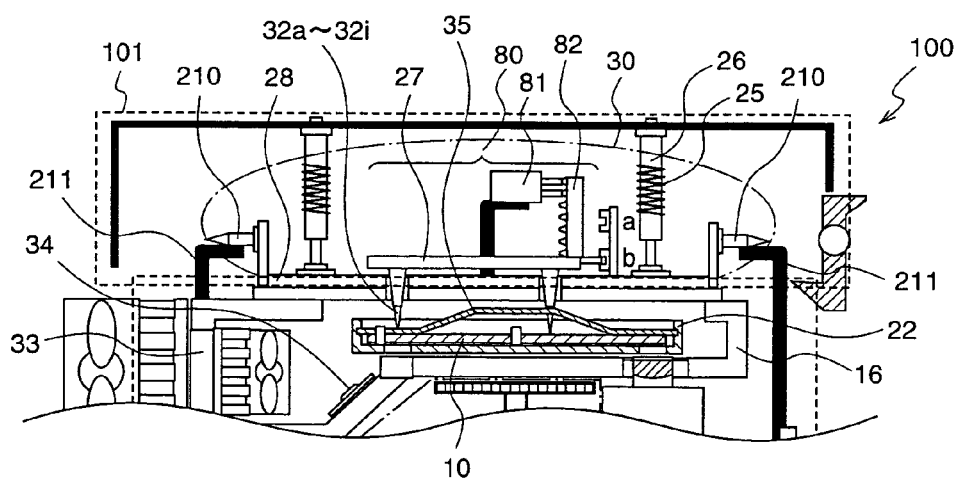
Figure 7:
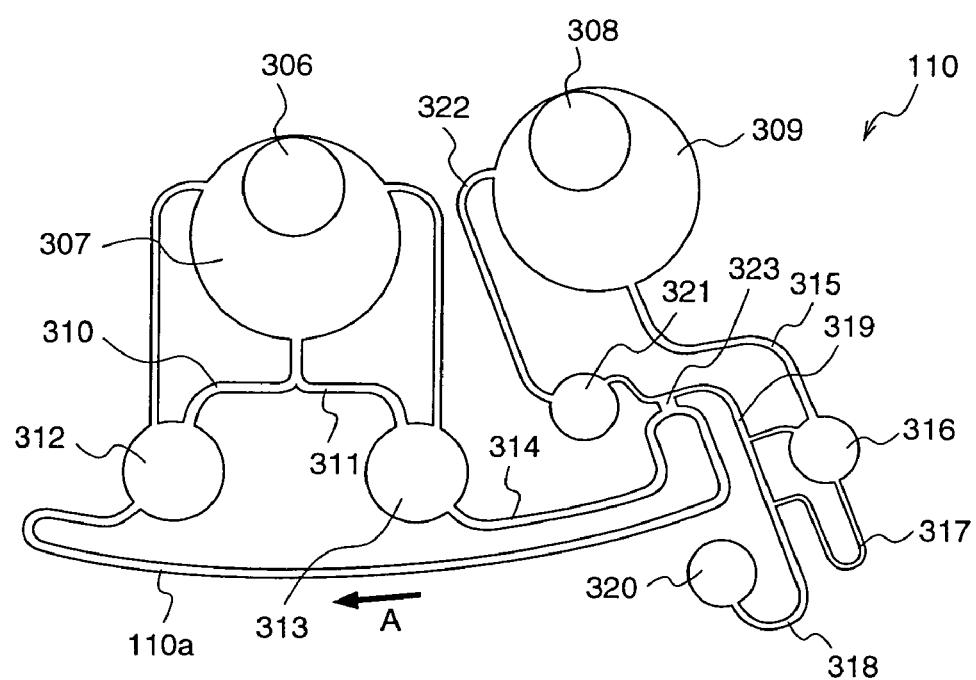
FIG. 7 is a diagram illustrating a channel formed on the plate according to the first embodiment.

FIGS. 6(a) and 6(b) are diagrams illustrating the state where a portion of the power supply application means is vertically moved by the voltage application contact/separation means. To be specific, FIG. 6(a) shows the state where the electrode probes are separated from the plate, and FIG. 6(b) shows the state where the electrode probes contact the plate. When voltage is applied to the plate 10 by the electrode probes 32 of the voltage application means 30, initially the electrode probe substrate 27 positioned at position "a" of the electrode height detection sensor 80 (refer to FIG. 6(a)) is moved to position "b" of the electrode height detection sensor 82 by driving the substrate 27 with the driving motor 81 of the voltage application contact/separation means 80 (refer to FIG. 6(b)). Thereby, the respective electrode probes 32 electrically contact the respective electrodes (not shown) on the plate 10 through the probe holes 35a of the plate clamp 35.

After the voltage application by the voltage application means 30 is completed, the driving motor 81 of the voltage application contact/separation means 80 is again operated to move the electrode probe substrate 20 from the position "b" to the position "a" of the electrode height detection sensor 82. Thereby, the respective electrode probes 32 that are in contact with the respective electrodes (not shown) on the plate 10 are separated from the plate 10.

The casing of the electrophoresis apparatus 100 according to the first embodiment comprises an upper chassis 101 and a lower chassis 102, and all the above-mentioned constituents are disposed in the casing. To be specific, the plate temperature control chamber 16 is disposed in the lower chassis 102, and the optical detection part 40 and the tray driving means 20 are disposed beneath the plate temperature control chamber 16. On the other hand, the voltage application means 30 is disposed in the upper chassis 101 such that it is latched through guide shafts 26.

Hereinafter, a description will be given of the positional relationship between the voltage application means 30 and the upper chassis 101, and the positional relationship between the voltage application means 30 and the lower chassis 102.

The voltage application means 30 and the upper chassis 101 are connected via the guide shafts 26 as described above, and an end of each guide shaft 26 is connected to the upper chassis 101 while the other end thereof is connected the base plate 28 of the voltage application means 30.

The length of the guide shafts 26 is selected such that, when the upper chassis 101 is closed, the base plate 28 is positioned with a slight overstroke with respect to the upper surface of the plate temperature control chamber 16. Further, each guide shaft 26 is provided with a compression spring 25 as an elastic member which is coaxial with the shaft 26. The lower chassis 102 is provided with positioning pin receivers 211 which receive positioning pins 210 provided on the base plate 28 of the voltage application means 30.

Figure 2:
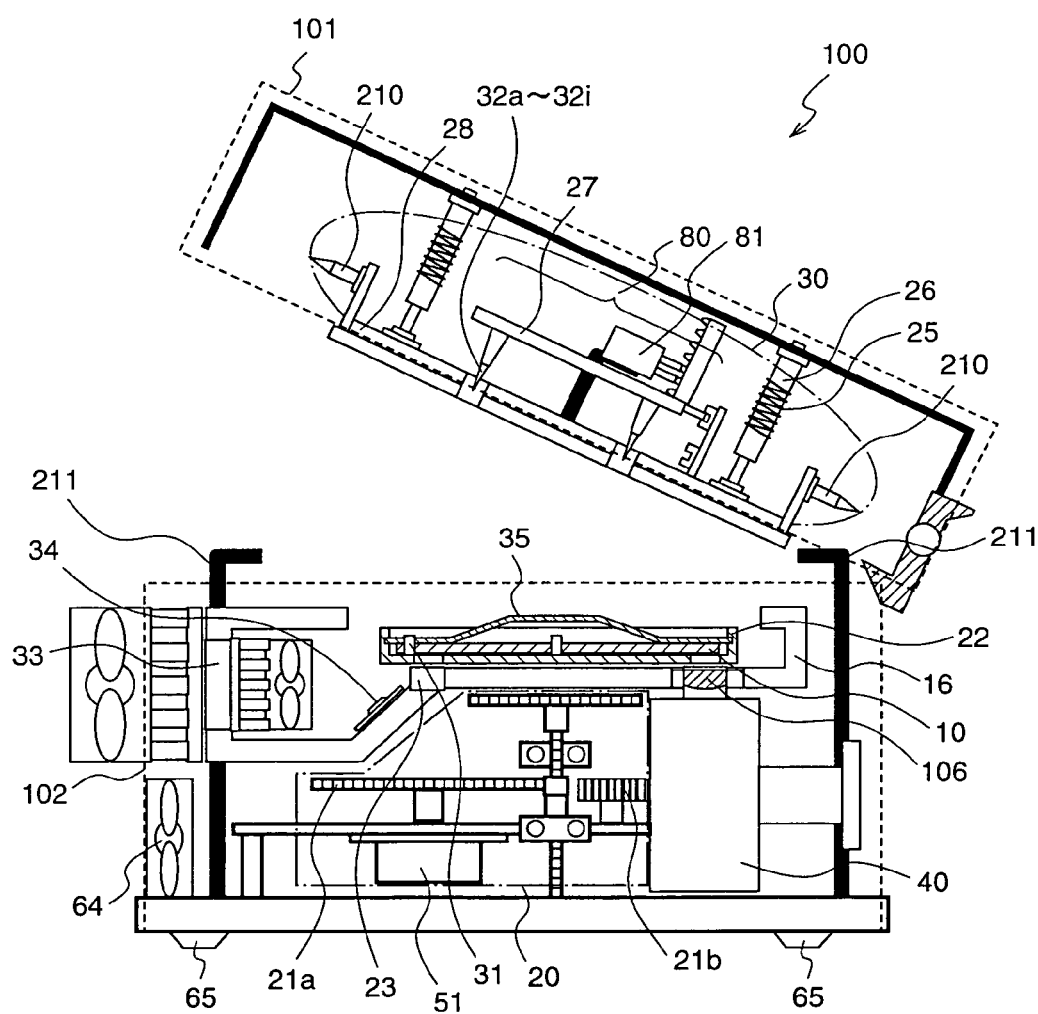
FIG. 2 is a diagram illustrating the electrophoresis apparatus according to the first embodiment, with an upper chassis being opened.

Accordingly, when the operation of opening the upper chassis 101 is carried out, as shown in FIG. 2, the voltage application means 30 that is latched to the upper chassis 101 via the guide shafts 26 is moved with the upper chassis 101 to a position that is sufficiently apart from the plate temperature control chamber 16, whereby the plate 10 can be taken out of or set on the tray 22 through the aperture of the plate temperature control chamber 16. Conversely, when the operation of closing the upper chassis 101 is carried out, the base plate 28 of the voltage application means 30 contacts the aperture of the plate temperature control chamber 16 and functions as a lid member, and thereafter, the base plate 28 is pressed against the aperture of the plate temperature control chamber 16 by the compression springs 25 of the guide shafts 26 until the positioning pins 210 contact the positioning pin receivers 211, whereby the plate temperature control chamber 16 is hermetically closed to prevent leakage of the temperature-controlled air in the control chamber 16.

As described above, when the upper chassis 101 is closed, since the entire voltage application means 30 is pressed against the lower chassis 102 by the compression springs 25 of the guide shafts 26, the voltage application means 30 is being pressed in the direction where it is separated from the plate 10. In this state, the electrode substrate 27 is moved down by the voltage application contact/separation means 80, and the respective electrode probes 32 are pressed against the predetermined positions on the plate 10 through the embedded springs 85, and then voltage application is carried out. Accordingly, during the voltage application, the respective electrode probes 32 of the voltage application means 30 are pressed in the direction where they are separated from the plate 10, in two stages, by the two elastic members, i.e., the embedded springs 85 provided at their front ends and the compression springs 25 of the guide shafts 26.

At this time, if the elastic force of the embedded springs 85 of the electrode probes 32 is larger than the elastic force of the compression springs 25 of the guide shafts 26, the positioning pins 210 provided on the voltage application means base plate 28 are undesirably lifted up from the positioning pin receivers 211 provided in the lower chassis 102. As a result, the entire voltage application means 30 is pressed in the direction where it is apart from the plate 10, and the pressing force of the electrode probes 32 to the electrodes on the plate 10 is decreased, whereby the contact resistance between the electrode probes 32 and the electrodes on the plate 10 is increased, or imperfect contact occurs, resulting in a defect that accurate voltage cannot be applied during electrophoresis. Accordingly, in this first embodiment, the total of the elastic forces that occur when the embedded springs 85 are subjected to predetermined deflection is set smaller than the total of the elastic forces which occur when the compression springs 25 that latch the voltage application means 30 are subjected to predetermined deflection.

The electrophoresis apparatus 100 further includes, directly under the tray 22, a plate position confirmation sensor 23 for confirming the position of the plate 10 on the tray 22, a high voltage power supply (not shown) connected to the electrode probes 32a~32i of the voltage application means 30, a control substrate (not shown) for controlling the operation of the whole apparatus 100, an apparatus power supply (not shown), a power supply switch (not shown) for controlling on and off of the apparatus, an LED (not shown) that is turned on when the power supply switch is in its ON state, a cooling fan 64 for cooling the inside of the apparatus 100, and a height-adjustable rubber legs 65 for protecting the apparatus 100 from vibration.

Next, a description will be given of an example of a channel 110 that is formed of grooves having minute widths and depths. In this first embodiment, eight channels 110 of the same shape are concentrically provided on the plate 10. The channel 110 has a conjugate inlet 306, and a sample inlet 308, and a DNA conjugate for separation that is injected from the conjugate inlet 306 is temporarily held in a conjugate injection part 307 while a DNA sample injected from the sample inlet 308 is temporarily held in a sample injection part 309. Further, reference numeral 312 denotes a positive electrode part into which a positive electrode is inserted, and numeral 313 denotes a negative electrode part into which a negative electrode is inserted. These electrodes are connected with each other through the channel 314, and are connected to the conjugate injection part 307 through the channels 310 and 311. Further, a conductive film 12 (refer to FIG. 3(*c*)) is attached to the positive electrode part 312 and the negative electrode part 313. When the electrode probes 32 contact the film 12 and thereby voltage is applied to the film, voltage is applied to the DNA conjugate for separation that is filled in the electrode parts 312 and 313. Reference numerals 316, 320, and 321 denote a chamber part, a sample holding part, and a buffer part, respectively, and the chamber part 316 is connected to the sample injection part 309 through the channel 315, the sample holding part 320 is connected to the chamber part 316 through the channels 317 and 318, and the buffer part 321 is connected to the chamber part 316 and to the sample holding part 320 through the channels 317, 318, and 319. Further, the buffer part 321 can be purged by the channel 322. Reference numeral 323 denotes a sample quantitation part, which is disposed in a position where the channel 314 and the channel 319 join together, and performs quantitation of the DNA sample.

A description will be given of a sequence of operations in the case where discrimination of SNPs in a DNA sample is performed by the electrophoresis apparatus 100 using the plate 10 on which the channels 110 are formed as described above.

Initially, the upper chassis 101 of the apparatus 100 is opened, and the plate 10 on which the DNA conjugate for separation and the DNA sample are injected into the channels 110 is set on the tray 22 in the plate temperature control chamber 16 through the aperture of the control chamber 16. At this time, the fitting pin 31 of the tray 22 is inserted in the fitting hole 11 of the plate 10, whereby the plate 10 is positioned with respect to the tray 22. Thereafter, the plate clamp 35 is put on the plate 10 disposed on the tray 22, and the projections 37 of the plate clamp 35 are fitted to the latch portions 41 of the tray 22, whereby the plate 10 is fixed to and held on the tray 22.

Then, the upper chassis 101 of the apparatus 100 is closed, and the plate temperature control chamber 16 is hermetically sealed by the base plate 28 of the voltage application means 30 that is attached to the upper chassis 101 via the guide shafts 26. At this time, the voltage application means base pate 28 is being pressed against the plate temperature control chamber 16 by the compression springs 25 provided on the guide shafts 26.

When the plate temperature control chamber 16 is thus hermetically closed, the thermistor 34 and the heating/cooling device 33 control the temperature inside the plate temperature control chamber 16 to a predetermined temperature.

Figure 8A:
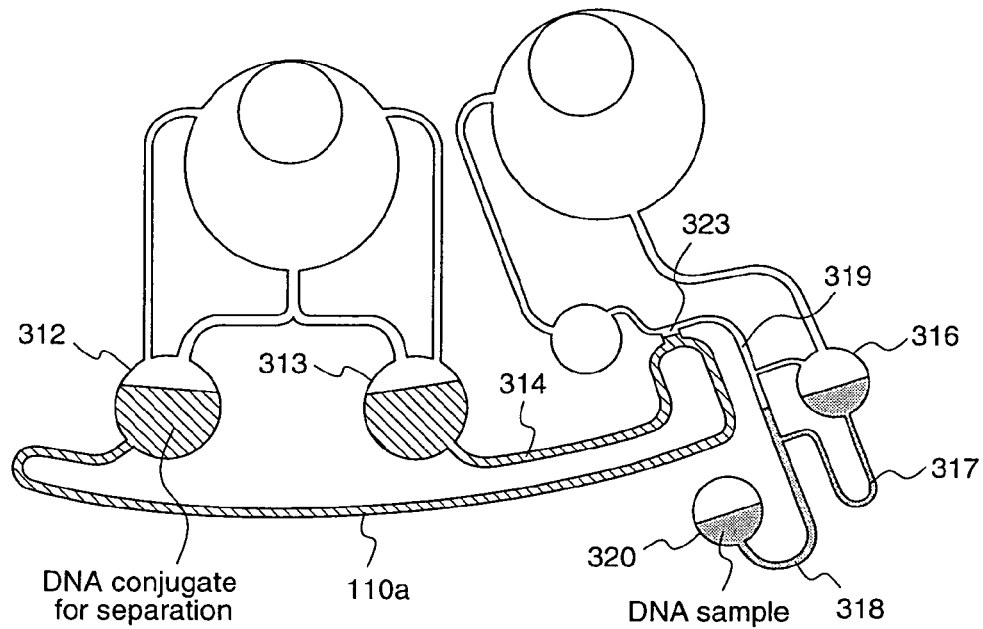
FIG. 8(*a*) is a diagram illustrating the state where a DNA conjugate for separation is filled in the channel formed on the plate according to the first embodiment.
Figure 8B:
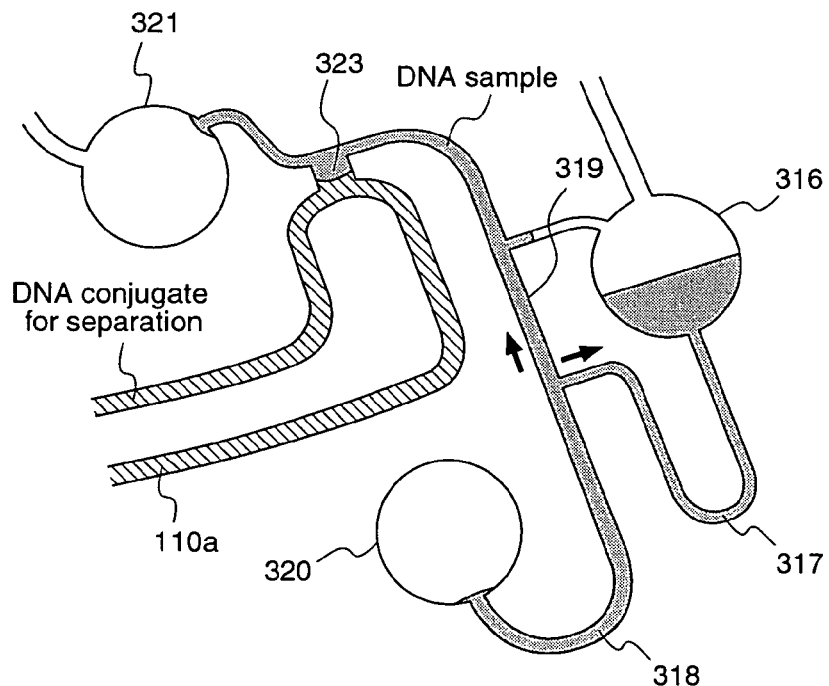
Figure 8C:
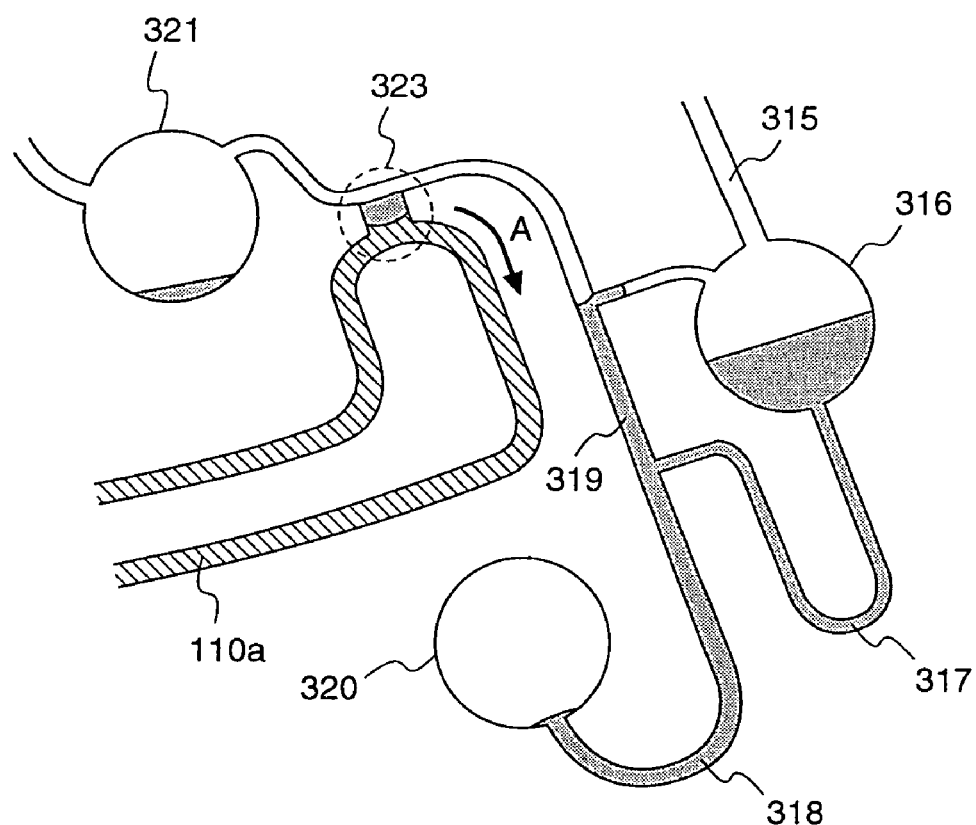

Next, the tray 22 is rotated at a high speed, whereby the DNA conjugate for separation added to the plate 10 is filled in the electrophoresis channel 110a, and simultaneously, a predetermined amount of the DNA sample is added to the filled DNA conjugate for separation in the sample quantitation part 323. To be specific, in this first embodiment, after the tray 22 is rotated at a high speed for a predetermined period of time by the tray driving means 20, the rotation is suddenly stopped, and then the tray 22 is again rotated at a medium speed for a few seconds. FIGS. 8(*a*)-8(*c*) illustrate the migration states of the DNA conjugate for separation and the DNA sample which are injected into the plate 10 according to the first embodiment, and specifically, FIG. 8(*a*) illustrates the state when a predetermined period of time has passed from the start of high-speed rotation, FIG. 8(*b*) illustrates the state immediately after the sudden stop of the high-speed rotation, and FIG. 8(*c*) illustrates the state after the medium-speed rotation.

The DNA sample that remains in the sample quantitation part 323 after the filling process becomes the final sample to be subjected to discrimination of SNPs. Then, the DNA sample is migrated electrophoretically by the voltage application means 30, and the DNA sample in the channels 110a is irradiated with light emitted from the optical detection part 40 to detect the intensity of luminescence (fluorescence) from the DNA sample by the optical detection part 40.

In this first embodiment, sequence control for performing the voltage application by the voltage application means 30 and the optical detection by the optical detection part 40 not simultaneously but alternately is carried out.

To be specific, initially the electrode probes 32a~32i of the voltage application means 30 are moved down to a predetermined position by the driving motor 81 of the voltage application contact/separation means 80 to bring the electrode probes into contact with the film 12 attached to the surface of the plate 10, and voltage is applied to the positive electrode part 312 and the negative electrode part 313 in the channel 110 for a predetermined period of time. After the predetermined period has passed, the electrode probes 32 are moved up to a predetermined position by the driving motor 81 of the voltage application contact/separation means 80, and in this state, the tray 22 is rotated at a low speed by the tray driving means 20 to read the intensity of fluorescence. That is, in this first embodiment, the electrophoresis and the optical detection are not simultaneously proceeded, but the optical detection by the optical detection part 40 is stopped during the voltage application by the voltage application means 30, and the voltage application by the voltage application means 30 is stopped during the optical detection by the optical detection part 40.

Thereby, since the mechanism for integrally rotating the voltage application means 30 and the tray 22 is dispensed with, the construction of the apparatus 100 can be simplified. Further, since the operation of supplying the high voltage for electrophoresis from the voltage application means 30 to the plate 10 and the operation of rotating the plate 10 are sequentially carried out, the voltage supply mechanism can be simplified.

In this first embodiment, the above-mentioned electrophoresis operation is carried out by making the electrode probes 32 contact the positive electrode part 312 and the negative electrode part 313 in the channel 110, and applying several hundreds of volt. Thereby, the DNA sample in the plate 10 electrophoretically migrates in the DNA conjugate for separation that is filled in the electrophoresis channel 110a, and travels in the channel 110a in the direction A. During this migration, the DNA sample migrates electrophoretically while repeating bonding with the DNA conjugate for separation. At this time, since bonding force of the normal DNA in the DNA sample with the DNA conjugate for separation is strong, the electrophoresis speed is low. On the other hand, since the bonding force of the mutant DNA in the DNA sample with the DNA conjugate is weak, the electrophoresis speed is higher than that of the normal DNA. That is, when both the normal DNA and the mutant DNA exist in the DNA sample, the normal DNA and the mutant DNA are separated from each other, whereby discrimination of SNPs can be carried out.

Figure 9:
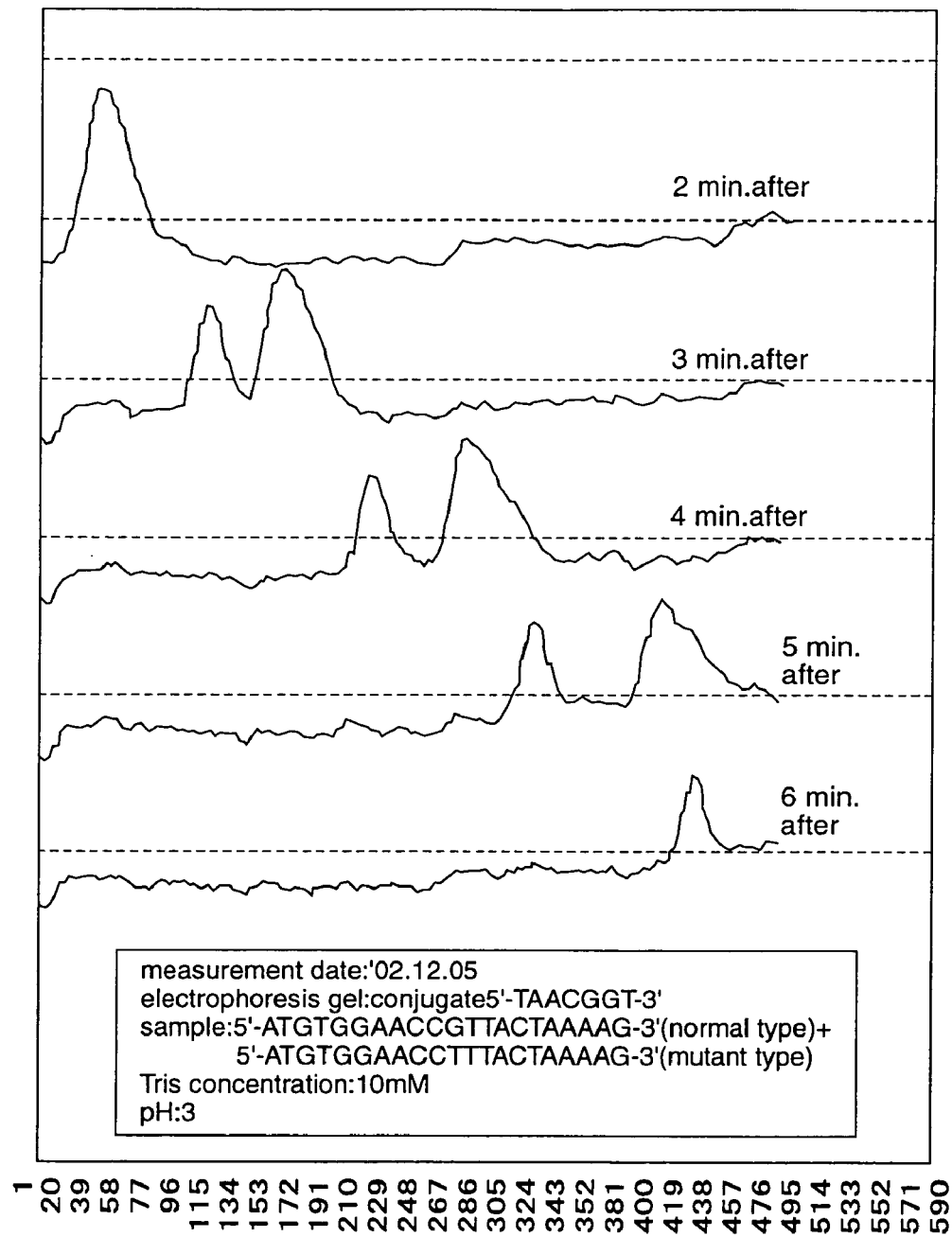
FIG. 9 is a diagram illustrating the fluorescence intensity distribution which is obtained when the DNA sample migrates in the DNA conjugate for separation that is filled in the channel formed on the plate according to the first embodiment.
Figure 10:
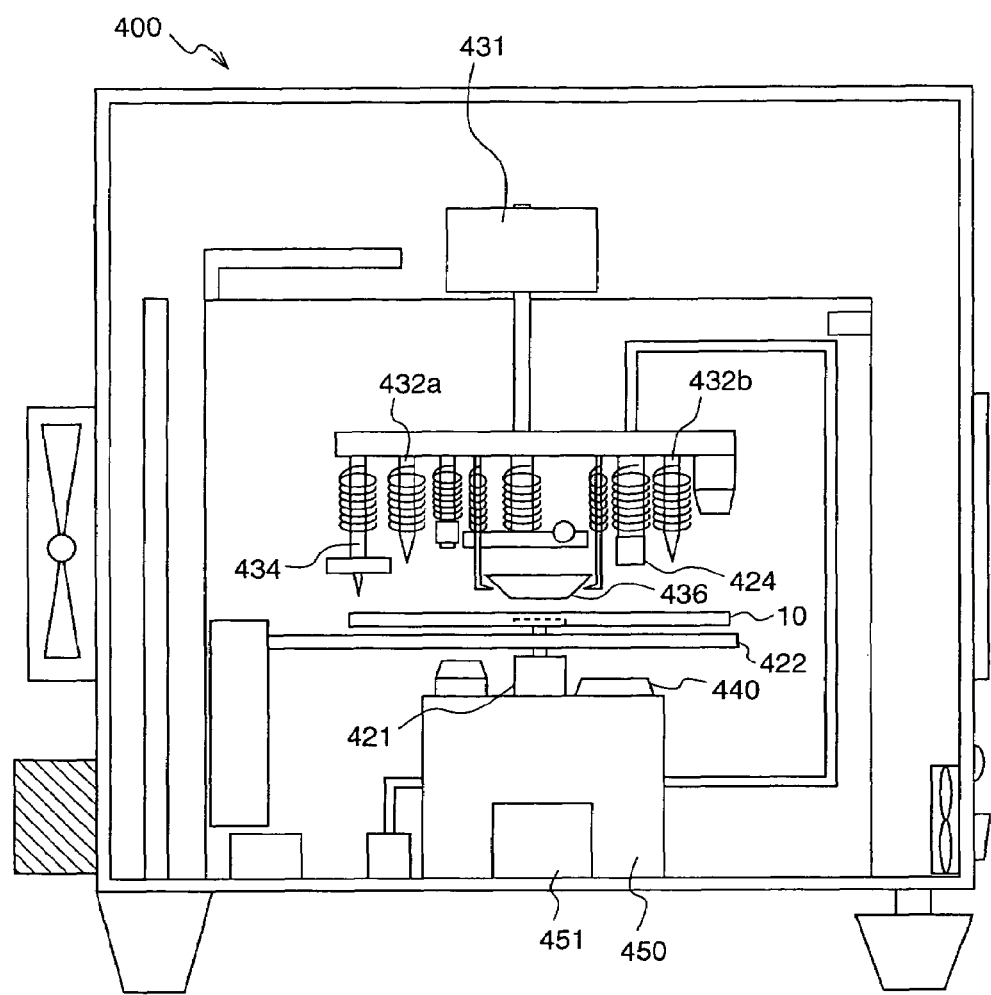
FIG. 10 is a diagram illustrating an example of a conventional electrophoresis apparatus.

Further, the above-mentioned optical detection is carried out by exciting the fluorescent-labeled (e.g., FITC) DNA with light of 470 nm, and performing photo detection in the vicinity of 520 nm. FIG. 9 is a graph illustrating the DNA sample migration state obtained at this time. The abscissa indicates the position on the electrophoresis channel 110a where optical detection is carried out, and the DNA migrates from left to right. That is, the left side is the sample quantitation part 323, and the right side is the positive electrode part 312. The ordinate indicates the fluorescence intensity, illustrating the waveform that changes with time for every one minute. It is evident from FIG. 9 that two peaks are gradually separated. The peak on the right side of the graph shows the mutant DNA having a relatively high electrophoresis speed, and the peak on the left side is the normal DNA having a relatively low electrophoresis speed. That is, in this case, it is determined that the same quantity of normal DNA and mutant DNA exist in the DNA sample. The above-mentioned detection may be performed using absorbance of 260 nm.

After the optical detection operation by the optical detection part 40 is completed, the plate 10 after the measurement is taken out of the tray 22 in the plate temperature control chamber 16. In this case, the upper chassis 101 of the apparatus 100 is opened, and the voltage application means 30 that is latched to the upper chassis 101 is moved back to a position that is sufficiently apart from the plate temperature control chamber 16 to expose the tray 22, and then the plate 10 is taken out of the tray 22.

As described above, in the electrophoresis apparatus 100 according to the first embodiment, the plate clamp 35 for holding and fixing the plate 10 to the tray 22 is disposed on the tray 22 on which the plate 10 is set, and only the portions of the plate 10 in the vicinity of the areas where the electrophoresis channels 110a are formed are held down by the plate clamp 35. Therefore, warpage or lifting of the plate 10 is efficiently suppressed, and the distance precision between the electrophoresis channels 110a on the plate 10 and the optical detection part 40 can be accurately achieved, resulting in accurate detection results.

Further, after the electrode probes 32 as the voltage application electrodes of the voltage application means are brought into contact with the desired positions on the plate 10, the sample in the plate 10 is electrophoretically migrated by voltage application, and the electrode probes 32 as the voltage application electrodes of the voltage application means are separated from the desired positions on the plate 10, and thereafter, the tray 22 on which the plate 10 is set is rotated to perform sequential control for optically detecting the sample on the plate 10 with the optical detection part. Therefore, the mechanism for integrally rotating the voltage application means 30 and the tray 22 on which the plate 10 is set during the optical detection is dispensed with, whereby the construction of the electrophoresis apparatus is simplified and miniaturized, and discrimination of the biological sample by the optical detection of the sample can be carried out in relatively short time.

Furthermore, sequential control is carried out such that the rotation of the tray 22 on which the plate 10 is set and the optical detection by the optical detection part are stopped during the voltage application by the voltage application means, while the voltage application by the voltage application means is stopped during the rotation of the tray 22 on which the plate 10 is set and the optical detection by the optical detection part are carried out. Therefore, the voltage application means, the tray driving means 20 for rotating the tray 22, and the mechanism for supplying power to the optical detection part can be simplified.

Furthermore, according to the electrophoresis apparatus 100 of the first embodiment, the optical detection part 40 and the tray driving means 20 are disposed outside the plate temperature control chamber 16 to minimize the volume of the plate temperature control chamber 16 that surrounds the plate 10 and the tray 22, and only the objective lens 106 of the optical detection part 40 is disposed in the plate temperature control chamber 16. Therefore, more accurate temperature control performance can be realized in the plate temperature control chamber 16, thereby providing highly reliable optical detection results.

An electrophoresis apparatus of the present invention is useful as one which can perform discrimination of a biological sample such as a DNA sample inexpensively and easily.

What is claimed is:

1. An electrophoresis apparatus for adding a sample into channels, making the sample migrate electrophoretically by voltage application, and optically detecting the sample, said apparatus comprising:
   a plate on which the channels are formed;
   a tray on which said plate is set;
   a voltage application unit having voltage application electrodes for applying voltage to a sample in the channels on said plate;
   a tray driving unit for rotary driving said tray on which said plate is set;
   an optical detection part having a light irradiation unit for irradiating the sample in the channels with light, and an optical detection unit for detecting light which is emitted from the sample when the sample is irradiated with the light from the light irradiation unit;
   a plate holding member for pressing only the channel formation areas of said plate against a plate setting surface of said tray, thereby fixing and holding said plate on the plate setting surface of said tray; and
   a voltage application contact/separation unit for making the voltage application electrodes of said voltage application unit contact with or apart from predetermined positions of said plate;
   wherein the voltage application electrodes of said voltage application unit are brought into contact with the predetermined positions of said plate by said voltage application contact/separation unit to make the sample migrate electrophoretically by voltage application, and thereafter, the voltage application electrodes of said voltage application unit are separated from the predetermined positions of said plate by said voltage application contact/separation unit, and the light emitted from the sample in the channels on said plate is detected by the optical detection part, and
   wherein said plate holding member has a convex configuration in which its center portion projects relative to its circumference portion, and presses said plate against the plate setting surface of said tray by the circumference portion.

2. An electrophoresis apparatus as defined in claim 1 wherein a predetermined amount of the sample is added to a buffer agent filled in the channels, and voltage is applied to the buffer agent by the voltage application electrodes of said voltage application unit to make the sample migrate electrophoretically.

3. An electrophoresis apparatus as defined in claim 1 further comprising:
   a temperature control chamber for controlling the temperature surrounding said plate to a predetermined temperature.

4. An electrophoresis apparatus as defined in claim 1 wherein the optical detection unit detects fluorescence that is generated from the sample due to light irradiation.

5. An electrophoresis apparatus as defined in claim 3 wherein said temperature control chamber contains said tray, and a heating/cooling device for controlling the plate temperature at a predetermined temperature, and has an aperture through which said plate can be attached/detached to/from said tray, the aperture being closed by a partial element of said voltage application unit which is disposed on said temperature control chamber.

6. An electrophoresis apparatus as defined in claim 5 wherein said voltage application unit has plural first elastic members which press partial members of said voltage application unit at predetermined positions against said temperature control chamber.

7. An electrophoresis apparatus as defined in claim 1 wherein the voltage application electrodes of the said voltage application unit are brought into contact with or apart from predetermined positions of said plate by said voltage application contact/separation unit, in the state where the aperture of said temperature control chamber through which said plate can be attached/detached to/from said tray is closed with a partial element of said voltage application unit.

8. An electrophoresis apparatus as defined in claim 3 wherein an optical lens constituting a part of the optical detection unit is disposed in said temperature control chamber.

9. An electrophoresis apparatus as defined in claim 1 wherein said plate setting surface of said tray has plural apertures so that the light which is emitted from the light irradiation unit to said plate is not obstructed.

10. An electrophoresis apparatus as defined in claim 9 wherein the plural apertures are provided on said tray at areas where the light radiated to the channels that are formed on said plate is not obstructed.

11. An electrophoresis apparatus as defined in claim 6 wherein the voltage application electrodes of said voltage application unit comprise probes having plural second elastic members for pressing the probes against said plate, the plural second elastic members being embedded in the probes, and said probes applying voltages to predetermined positions of the channels formed on said plate.

12. An electrophoresis apparatus of defined in claim 11 wherein
   a total of elastic forces of the plural first elastic members that elastically support an entire mechanism of said voltage application unit is larger than a total of elastic forces of the plural second elastic members that are embedded in the probes as the voltage application electrodes, and
   said voltage application unit is pressed in a two-stage construction by the plural first elastic members and the plural second elastic members, in the direction where said voltage application unit presses said plate or in the direction where said voltage application unit is separated from said plate.

* * * * *